United States Patent [19]
Bonnet et al.

[11] Patent Number: 5,978,708
[45] Date of Patent: Nov. 2, 1999

[54] DETECTION AND CONFIRMATION OF CROSS-SENSING PHENOMENON IN ACTIVE IMPLANTABLE MEDICAL DEVICES

[75] Inventors: Jean-Luc Bonnet, Montrouge; Laurence Geroux, Chatenay, both of France

[73] Assignee: ELA Medical S.A., Montrouge, France

[21] Appl. No.: 09/067,812

[22] Filed: Apr. 28, 1998

[30] Foreign Application Priority Data

Apr. 29, 1997 [FR] France .................................. 97-05286

[51] Int. Cl.⁶ ...................................................... A61N 1/37
[52] U.S. Cl. .............................................................. 607/14
[58] Field of Search ........................................... 607/9, 14

[56] References Cited

U.S. PATENT DOCUMENTS

| | | | |
|---|---|---|---|
| 4,967,746 | 11/1990 | Vandegriff | 128/419 |
| 5,167,224 | 12/1992 | Limousin et al. | 128/419 |
| 5,226,415 | 7/1993 | Girodo et al. | 128/419 |
| 5,247,929 | 9/1993 | Stoop et al. | 607/14 |

FOREIGN PATENT DOCUMENTS

| | | | |
|---|---|---|---|
| 0 562 237 | 9/1993 | European Pat. Off. | A61N 1/368 |
| 0 705 620 | 4/1996 | European Pat. Off. | A61N 1/36 |
| 2 668 372 | 4/1992 | France | A61N 1/362 |

*Primary Examiner*—William E. Kamm
*Attorney, Agent, or Firm*—Orrick, Herrington & Sutcliffe LLP

[57] ABSTRACT

An active implantable medical device, especially of a cardiac pacemaker, defibrillator and/or cardiovertor type, having a dual chamber stimulation function and protection against cross-sensing atrio-ventricular phenomena. Cardiac events, spontaneous or stimulated, are detected in a first cavity, preferably the atrium, and a second cavity is stimulated, preferably the ventricle, The detection and confirmation of cross-sensing is performed by detecting in the atrium a signal coming from a depolarization consecutive to a preceding stimulation of the ventricle, and distinguishing such a signal from a signal resulting from spontaneous activity of the atrium. According to an embodiment, the detection of cross-sensing preferably includes the detection of an activity of the atrial extra-systole type occurring between a ventricular stimulation and a consecutive atrial event, stimulated or spontaneous, in order to determine that the interval of time between the stimulation of the second cavity and the atrial extra-systole type is less than a predetermined duration, and to detect the stability of this interval, preferably by modulating the atrio-ventricular delay (AVD) and to detect the absence of significant modification, with regard to these variations, in a particular time interval in question.

17 Claims, 4 Drawing Sheets

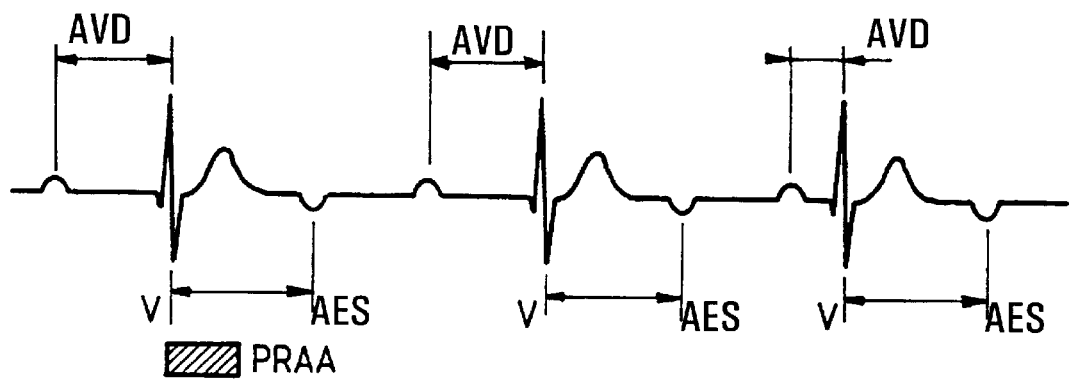
FIG_1A
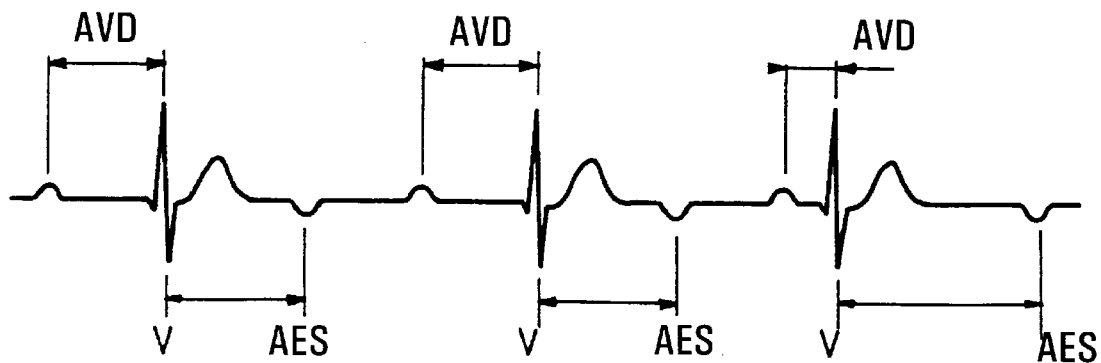
FIG_1B

FIG_3

DETECTION AND CONFIRMATION OF CROSS-SENSING PHENOMENON IN ACTIVE IMPLANTABLE MEDICAL DEVICES

FIELD OF THE INVENTION

The present invention concerns "active implantable medical devices" such those defined by the Directive 90/385/EEC of Jun. 20, 1990 of the European Community Council, more particularly devices such as cardiac pacemakers, defibrillators and/or cardiovertors having a double-chamber stimulation function for the processing of troubles of the atrial rhythm.

BACKGROUND OF THE INVENTION

Active implantable medical devices that collect (sense) and deliver (stimulate) signals in the atrium as well as the ventricle are subject to a disadvantage known as a "cross-talk" or "cross-sensing" phenomenon. This phenomenon occurs when, in the atrial cavity, the pacemaker detects a signal coming from a depolarization following a preceding ventricular stimulation (this cross-sensing phenomenon will be designated in the following as "CTVA" ("Cross-Talk Ventriculo-Atrial")). The device can wrongly interpret this signal as resulting from a spontaneous depolarization of the atrium, with the result that this detected phenomenon is prejudicial to the expected functioning of the device.

In current devices, this CTVA phenomenon is all the more emphasized because of the relatively greater the sensitivity of input amplifiers of the atrial stage; this high sensitivity is used to be able to sense and interpret signals of low amplitude in the atrium, in case of TdRA (Troubles of the Atrial Rhythm), a generic term that covers various atrial arrhythmia such as tachycardia, fibrillation, flutter, etc., which troubles are all characterized by a rapid, abnormal atrial rhythm at the detection.

To improve both the sensitivity and the selectivity of the atrial sensing and detection, it is therefore necessary to remedy the consequences of this cross-sensing.

A first solution concerns creating a time interval called "blanking", during which the atrial amplifier is completely disconnected from the sensing circuit during a ventricular stimulation (as described, for example, in U.S. Pat. No. 4,825,870 for an amplifier of signals detected in the ventricular cavity). But this blanking period is released (triggered) only during stimulation and has only a short duration; the former does not therefore, protect, against the delayed detection of the signal of depolarization.

EP-A-0 594 957 describes another manner to process the problem of the CTVA. It proposes to analyze collected signals and, when a signal in the atrium is detected at the same time that a signal is present on the ventricular stage, the device deduces from this concomitance that the detected atrial signal has its origin in the ventricle. Proceeding in this manner, however, suffers the disadvantage that one cannot detect spontaneous signals emitted by two cardiac cavities that are totally desynchronized. Further, such a processing of signals considers only the spontaneous events, and not the stimulated events.

Another solution would be to increase the atrial refractory period. This solution, although easy to implement in current pacemakers, would have the disadvantage to decrease the atrial sensing window. The rapid atrial arrythmias could then be partially detected, limiting the efficiency of the diagnosis algorithms.

Further, EP-A-0 705 620 describes a dynamic window technique so as to better recognize signals coming from a tachycardia, and to distinguish them from signals coming from a CTVA.

OBJECTS AND SUMMARY OF THE INVENTION

It is an object of the present invention to overcome the aforementioned disadvantages.

Essentially, the present invention proposes to recognize the CTVA phenomenon by observing the manner in which ventricular stimulation/atrial detection sequences occur. A repetition of such sequences will lead to a phase of "suspicion of the cross-sensing", that will in turn release a phase of "verification"; if the verification is positive, then the device will take measures to stop this CTVA phenomenon.

More preferably, the present invention proposes an active implantable medical device, especially a cardiac pacemaker, defibrillator and/or cardioverter, having a double-chamber stimulation function, this device comprising means for detecting cardiac events, spontaneous and/or stimulated events, in a first cavity, means for stimulating in a second cavity, and means for the detection and confirmation of cross-sensing, to detect in the first cavity a signal coming from a depolarization consecutive to a preceding stimulation of the second cavity, and to distinguish such a signal from a signal resulting from spontaneous contraction of the first cavity.

According to a preferred embodiment of the invention, the cross-sensing detection and confirmation means comprise means to detect an activity of the type "extra-systole" of the first cavity occurring between a stimulation of the second cavity and a consecutive event, stimulated or spontaneous, in the first cavity. In a further preferred embodiment, the first cavity is an atrial cavity and the second cavity is an associated ventricular cavity.

The cross-sensing detection and confirmation means advantageously comprises means for detecting an extra-systole of the first cavity occurring between a stimulation of the second cavity and a following consecutive event, stimulated or spontaneous, in the first cavity, to determine that the interval of time between the stimulation of the second cavity and the extra-systole of the first cavity is less than a predetermined duration, and to detect the stability of the interval of time between the stimulation of the second cavity and the detected extra-systole of the first cavity.

The means for detecting the stability preferably comprises means for varying the period between the detection of an event in the first cavity and the stimulation of the second cavity, and to detect the absence of significant modification, with regard to these variations, of the interval of time between the stimulation of the second cavity and the extra-systole of the first cavity.

In a preferred embodiment, the device can in addition comprise means for suppressing cross-sensing, by increasing the refractory period associated with the first cavity in case of detection and confirmation of a cross-sensing or, in another embodiment, reducing the sensitivity of the means for detecting cardiac events in the first cavity in case of detection and confirmation of a cross-sensing.

It is also foreseen to provide means for detecting the end of the cross-sensing phenomenon, and to restore to their initial or prior values the parameters of the device modified by the cross-sensing detection and confirmation means.

BRIEF DESCRIPTION OF THE DRAWINGS

Further characteristics, features and advantages of the invention will appear to a person of ordinary skill in the art in view of the following detailed description of a preferred embodiment of the prevent invention, with reference to the drawings annexed, in which:

FIGS. 1A and 1B illustrate, on an electrocardiogram trace waveform, the position of the different implemented periods and implemented refractory periods.

DETAILED DESCRIPTION OF THE INVENTION

Figure 2:
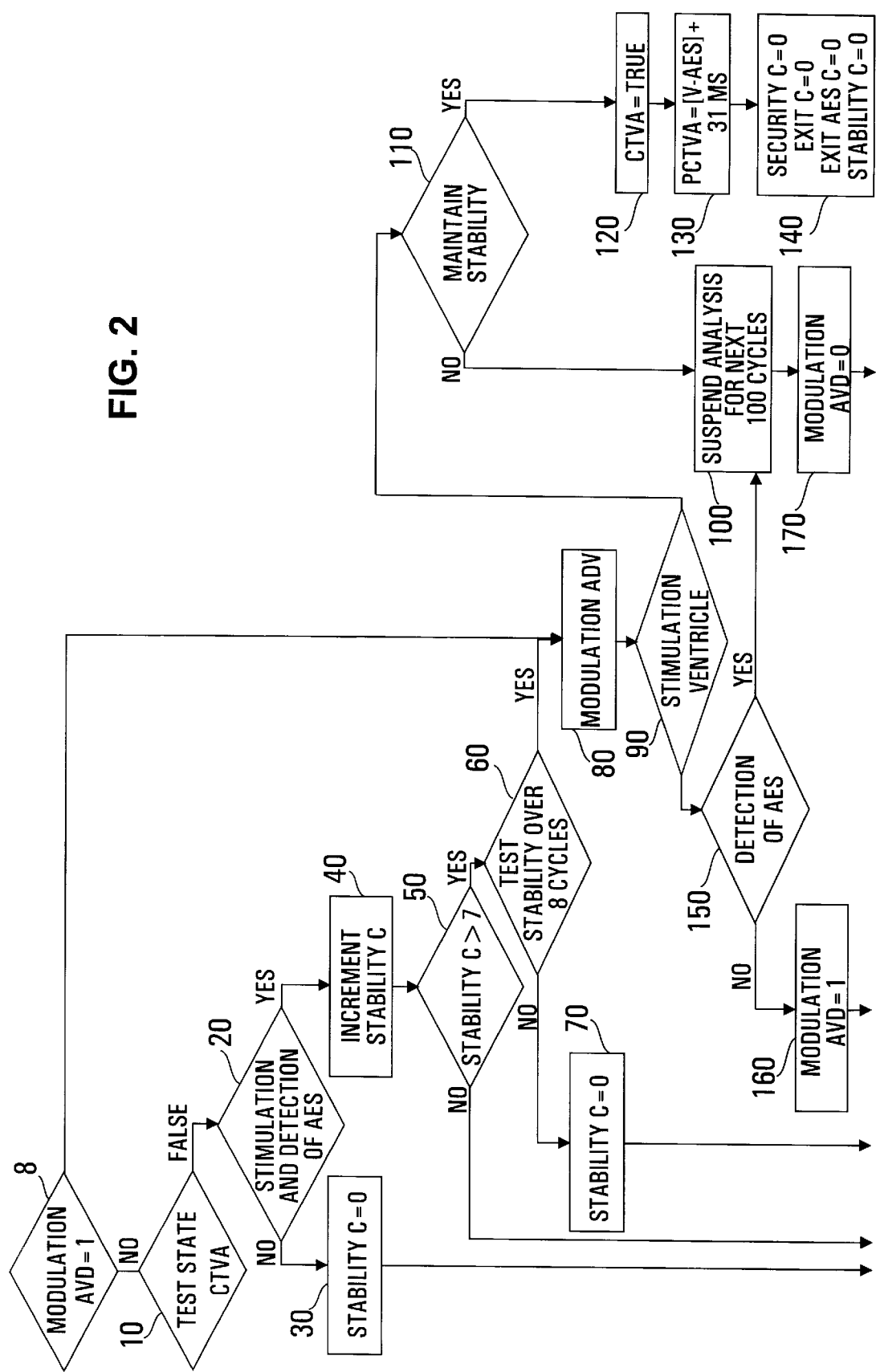
FIGS. 2 and 3 are flow charts illustrating the sequence of the various stages of a process implemented by the invention.

In the following discussion, one will consider the case of the atrial over-detection. Nevertheless, it would be possible to envisage also implementing the present invention in the case of the over-detection in the ventricular cavity, such that the reasoning presented for the atrial case may be applied to the ventricle in the same manner, mutatis mutandis.

As indicated above, a CTVA is an atrial over-detection: after a ventricular stimulation, in some conditions, one can detect on the atrial electrode a signal that is in fact only a "residue" of the ventricular stimulation. This detection occurs just after the Absolute Atrial Refractory Period (PRAA), such that it can be desirable to program a short period so as to optimize the atrial sensing in case of the presence of an atrial arrhythmia. These atrial detections, in the absence of a particular processing, are then considered, wrongly, as premature events being able to make a suspicion a trouble of the atrial rhythm ("TdRA").

The algorithm of the invention has for an object to insure a protection against CTVA: by diagnosing the appearance of the CTVA, and by operating a differentiation between CTVA and TdRA, and by maintaining, to the extent the possible, an optimal detection of the atrial arrythmias by avoiding to apply a long atrial refractory period in the absence of CTVA.

The algorithm that allows one to realize these functions comprises several phases:

1) a phase of detection, where one studies or researches the presence of a possible CTVA phenomenon, 2) a phase of confirmation, to discriminate between CTVA and TdRA, 3) a phase of suppression, to protect the device in case of a confirmed CTVA, and 4) a phase of restoration of the initial parameter at the sensing in case of the disappearance of the confirmed CTVA.

One is going now to describe in detail these phases.

THE PHASE OF DETECTION OF THE CTVA

In normal functioning, the device records the ventricular event sequence, especially the ventricular stimulation signal, and the atrial event sequence (the term "event" refers to either signals coming from a spontaneous depolarization, or signals resulting from stimulation impulses applied by the device). The device includes a circuit means for detecting an AES(Atrial Extra-Systole:) and a VES (Ventricular Extra-Systole) as described, for example in EP-A-0 676 217 and its corresponding U.S. Pat. No. 5,584,867 commonly assigned to ELA Medical. The U.S. Pat. No. 5,584,867 is incorporated herein by reference.

A P-wave (that is, sensing an event having its origin in the atrium) is defined as an AES if the interval of time separating the P-wave of the preceding atrial event is less than a fraction of the average PP interval, that is to say the average interval of the atrial frequency calculated over (typically) eight cardiac cycles not comprising an extra-systole.

The algorithm of the invention has for an object to notice, in the sequence of signals, premature P-waves resembling an AES. In the next phases, one will determine if it concerns a real AES, that is to say it is revealing signals of a TdRA by an abnormal acceleration of the rhythm, or a CTVA, therefore of a parasitic signal. In the latter case, and only in this case, one will take necessary measures to stop the parasitic character of the CTVA.

The CTVA is characterized by a succession of sequences V-AES-A or V-AES-P, these sequences repeating as long as the CTVA is present, and possibly with an alternation of these two sequences ("V"= stimulated ventricular wave; for "A"= stimulated atrial wave; and "P"= spontaneous atrial sinus wave). One can define three revealing characteristics for a CTVA:

a) presence of an AES for the ventricular cycle, for each of the two patterns;

b) stability of the interval V-AES, because this interval depends only on the ventricular depolarization (the criterion of stability can be the same as the one that one considers when one wishes to detect tachycardias induced by a re-entry phenomenon (TRE), as that is described for example in FR-A-2 54 988 and FR-A-2 668 372 (and its corresponding U.S. Pat. No. 5,167,224 which is commonly assigned and incorporated herein by reference), that as will be described hereafter in more detail);

c) a short interval V-AES, on the order 100 to 200 ms.

In this phase of detection, one is going to observe a certain number of consecutive ventricular cycles, and determine whether these three criteria are verified. Nevertheless, if these characteristics are necessary in order that one is in the presence CTVA, they still are not sufficient.

Indeed, some troubles of the atrial rhythm, such as tachycardia or atrial "flutter", also present these characteristics, the pacemaker functioning in this case in a 2:1 or 3:1 association mode.

PHASE OF CONFIRMATION OF THE CTVA

The phase "of confirmation" allows one to undertake a discrimination between the necessary and the sufficient conditions.

To confirm or not the CTVA, one can proceed by modulating the atrio-ventricular delay(AVD), because the CTVA is linked to the ventricular stimulation.

The modulation technique is known in a different application, that is the that algorithms "anti-TRE", as described in FR-A-2 54 988 and FR-A-2 668 372 (U.S. Pat. No. 5,167,224) aforementioned, where, after a phase of suspicion of TRE, one modulates the AVD so as to confirm that the observed trouble is actually a TRE and not a TdRA.

By applying this discrimination technique to the present case, as the inventors have realized as soon as the phase of detection has resulted in a suspicion of CTVA, the pacemaker modulates the AVD so as to determine if the interval of time V-AES remains stable or varies: in the first case (cf. FIG. 1A), it concerns a CTVA; in the opposite case (cf. FIG. 1B) it concerns a TdRA.

The modulation of the AVD depends on the state in which is found the pacemaker. If the AVD programmed for the device is at an upper limit at the time it is to be modulated then the modulation of the AVD is negative, that is to say that the AVD has to be decreased. In the opposite case, the AVD is increased.

If the interval of time V-AES remains stable in spite of this modulation of the AVD, one confirms the presence of the CTVA, and one passes to the next phase, that has for its object to protect the device against this parasitic CTVA event.

PHASE OF SUPPRESSION OF THE CTVA

From a confirmation of a CTVA, the pacemaker modifies its behavior so that the CTVA could not be interpreted as a consequence of a spontaneous contraction of the atrium. A first solution is to modify the refractory periods defined by the device by adding a relative refractory period Pctva, such that all atrial events detected in this window are considered as not being an AES and are not recorded as a AES. This refractory period Pctva is, for example, equal to the interval [V-AES]+31 ms, and has to be relative to allow the detection and the analysis of CTVA.

In another embodiment, another solution to protect the device against the consequences of the CTVA is simply to lower the sensitivity of the atrial detection, by increasing the threshold of detection, until there is a disappearance of the CTVA condition.

PHASE OF RESTORATION AFTER CTVA

The return to the normal functioning can intervene either by the spontaneous disappearance of the CTVA condition, or by testing at intervals, preferably at regular intervals, for the existence of the CTVA as to know if the former is always present, or by return to a spontaneous V activity.

A DETAILED IMPLEMENTATION

Figure 3:
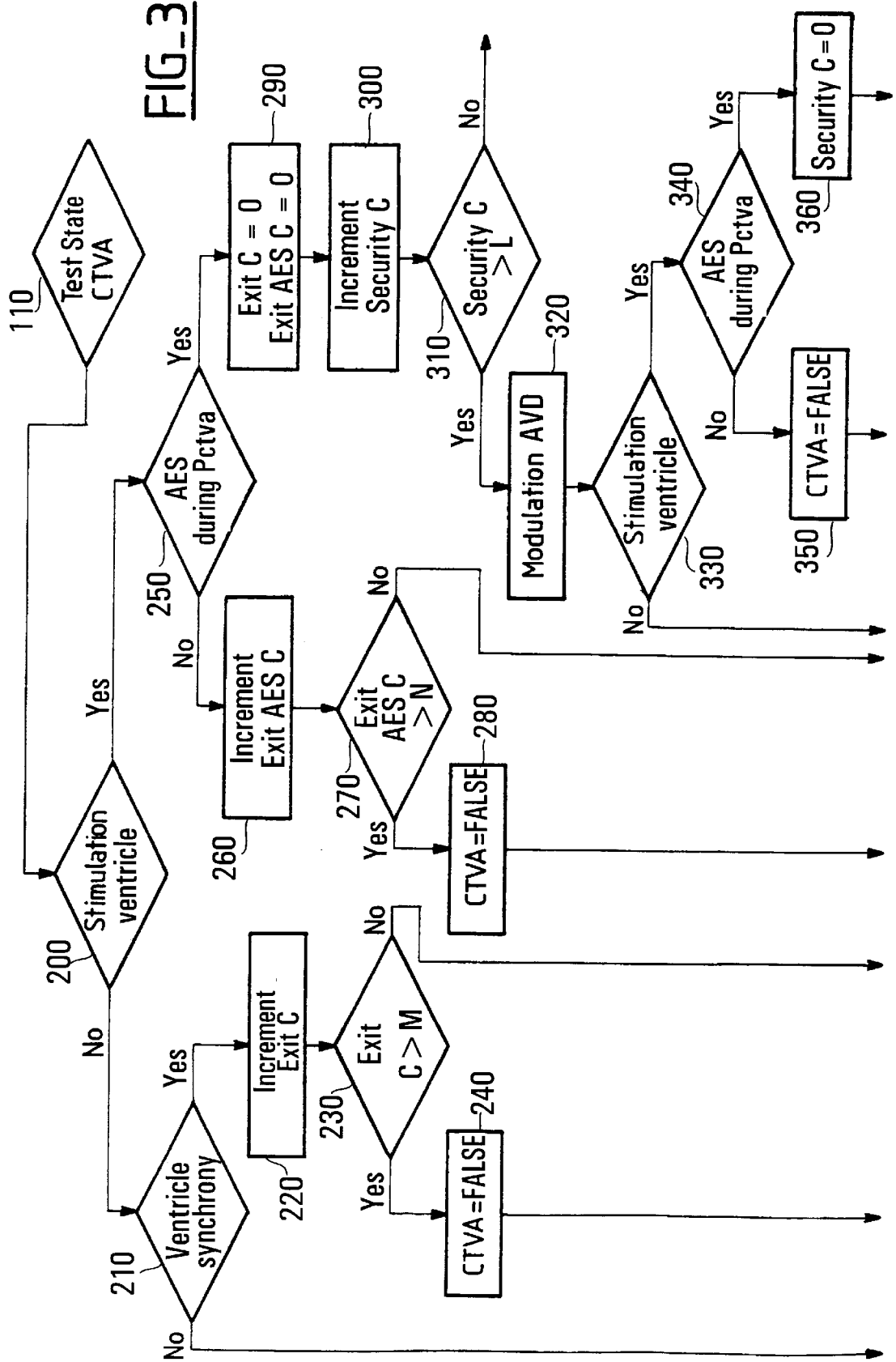

Referring to FIGS. 2 and 3, in consideration of the foregoing description, a flow chart of a preferred implementation of the principle of the algorithm described above in which the FIG. 2 corresponds to phases of detection and confirmation of CTVA, and FIG. 3 corresponds to the phase of suppression as shown.

The different variables and abbreviations used on these flow charts are following:

"CTVA": a binary variable, indicating the presence or the absence of a condition known as "Cross-talk VA";

"Pctva": a refractory period of the recovery of the CTVA, typically Pctva=[V-AES]+31 ms;

Stability C: a counter allowing one to test the stability of the detection of the CTVA over a number of cycles, preferably 8 cycles; this counter of stability serving solely to count eight consecutive cycles comprising a ventricular stimulation followed by an atrial detection (AES);

Security C: a counter of security, allowing after the diagnosis of a CTVA to test periodically the persistence of the CTVA phenomenon; therefore, in each Security C ventricular cycles, one modulates again the AVD so as to see if the CTVA phenomenon is always present;

Exit C: a counter of "exit" by reappearance of the spontaneous rhythm such that at the end of Exit C spontaneous ventricular cycles, one leaves the algorithm; indeed, there is no longer any CTVA condition if the ventricle is no longer stimulated;

Exit AES C: a counter of "exit" by disappearance of the CTVA: at the end of Exit AES C ventricular cycles stimulated without a CTVA detected in Pctva, one leaves the algorithm because the phenomenon has disappeared for a sufficient length of time (in a prolonged manner).

"Stimulation V and detection of an AES": a cycle with a ventricular stimulation and detection of an atrial event in relative refractory period (therefore an AES).

"stability Test over 8 cycles": Over the eight cycles, there must be at each cycle a ventricular stimulation followed by an atrial detection in refractory period (therefore of an AES); With this test, one wants to see if the period between the ventricular stimulation and the atrial detection is stable over the eight cycles.

"Modulation of the AVD": To confirm the CTVA, one wants to verify that the stability of the period between the ventricular stimulation and atrial detection depends solely on the ventricular stimulation and not on the preceding atrial event. For this, one modulates the AVD so as to change the period between the preceding atrial event and the ventricular detection.

"Maintenance of the stability": After the modulation, one looks if the period between the ventricular stimulation and the atrial detection is always identical.

Referring now to FIG. 2, the study of CTVA for the sequence of one cycle is shown. The diagnosis of CTVA (stage 10) in the case where there is no ongoing modulation from a prior cycle (the AVD flag is set equal to 0) (stage 8) is made in two steps, the first being the research of a stable interval [V-AES] (stage 20). If there is ongoing modulation (AVD flag=1) (stage 8), then the routine goes to the next modulation (stage 80).

To this end, one has to have over eight ventricular cycles (stage 60): a ventricular stimulation (stage 20) at each cycle (stage 50), one and only one AES at each cycle, and a stable interval [V-AES], typically at or about 16 ms over the eight cycles.

The second stage is the modulation of the AVD (stage 80). As soon as the conditions above are filled, one undertakes on the cycle following a modulation of the AVD to verify that the stability of the interval VP does not depend on the preceding atrial signal but solely of the ventricular stimulation. The modulation will be negative and of −31 ms (for example) if the AVD allows it, otherwise the modulation will be positive and of 31 ms (for example).

In a first time, one validates the modulation of the AVD (stage 90). If a ventricular detection occurs following the modulation (stage 90): If there is an AES detected (stage 150) after this ventricular event, then the diagnosis of CTVA is negative (it is probably a TdRA). If there is no AES then the stage of modulation of the AVD is reiterated (AVD flag=1) (stage 160) on the next cycle (stage 8) because no decision can be taken.

In the case of an asynchronous ventricular detection in the course of the cycle where one should have modulated, then the modulation is postponed to the following cycle and the analysis continues normally. If none of the two preceding cases is proven, the interval [V-AES] is analyzed on the modulated cycle.

If, following the modulation (stage 80), the ventricle is stimulated (stage 90) and the interval [V-AES] is identical to the interval calculated over 8 cycles (near to 16 ms) (stage 110), then the diagnosis of CTVA is positive (stage 120).

If, following the modulation, the ventricle is stimulated (stage 90) and the interval [V-AES] is different than the one that measured over 8 preceding cycles (near to 16 ms) (stage 110) then the diagnosis of CTVA is negative (stage 100) and the study of CTVA is forbidden during the next 100 cycles, and the modulation is ended and the AVD flag is reset to 0 (stage 170).

Then, if the diagnosis of CTVA is undertaken (a positive diagnosis) (stage 120): one calculates the value of a window of recovery of the CTVA (stage 130): Pctva=[V−AES]+31 ms, one initializes a counter Security C, allowing to control regularly if the diagnosis of CTVA is always verified. One initializes a counter Exit AES C that will condition the exit of the diagnosis of CTVA in case of the disappearance of a detection in Pctva. One initializes a counter Exit C, (stage 140) allowing to condition the exit of the diagnosis of CTVA in case of an appearance of a spontaneous conduction.

Referring to FIG. 3, the phase of restoration (functioning in a state CTVA and diagnosis of the end of CTVA) is disclosed.

When the device has detected a CTVA (stage 190) the general functioning is the same, more particularly, all algorithms are active. Only the refractory periods change.

Indeed, one adds to preceding periods the relative refractory period of CTVA designated by Pctva (FIG. 1). This relative refractory period is applied (stage 250) only after a ventricular stimulation (stage 200). It is no longer applied after a ventricular detection (stage 210), synchronous or not (stage 240).

The appearance of the CTVA is tested every ventricular cycle once the diagnosis of CTVA has been undertaken, this so as to favor a rapid return to normal functioning with an optimized refractory period. This research is undertaken only in a period of a 1:1 AV association.

The periodic persistence test of the CTVA has as its object to verify, once the CTVA is installed, that no error of diagnosis has happened in the beginning of the research. For this, one undertakes periodically a test of modulation. If the ventricle is stimulated (stage 200) and if a P wave is detected in Pctva (stage 250) then one increments a counter Csecurite (stage 300). As soon as this counter Csecurite exceeds a value L, for example L=1000 (stage 310), one tests again the appearance of a CTVA with the help of a modulation (stage 320). The AVD is modulated 31 ms, in the negative if possible, if after the modulation there is always a detection P in Pctva (stage 340), then CTVA remains set to true and Csecurite is set to zero (stage 360).

If there is no detection P in Pctva (stage 340), then CTVA is set to false (stage 350) and the device returns to the phase of research of CTVA (stage 10, FIG. 2).

The end of CTVA occurs by an end of the cross detection.

If the ventricle is stimulated (stage 200) and if no wave P is detected in Pctva (stage 250), then one tests the possibility of exit of CTVA by stopping of the TVA phenomenon. The counter Exit AES C (stage 260) is incremented and, as soon as this counter exceeds a value N, for example N=16, CTVA is set to false (stage 290) and the device returns a phase of research CTVA.

The end of CTVA also may occur by a return of the spontaneous conduction. If the ventricle is not stimulated (stage 200) and is synchronized (stage 210), then one tests the possibility of exit of CTVA by return of the spontaneous conduction (stage 210). The counter Exit C is incremented (stage 220) and, as soon as this counter exceeds a value M (stage 230), for example M=16, CTVA is set to false (stage 240) and the device returns to a phase of research of CTVA (when the conduction is spontaneous, Pctva is not applied).

As soon as the condition CTVA becomes false (stages 240, 280, 350), Pctva is set to zero and/or the atrial sensitivity is returned or reset to its initial value (programmed value). The two counters of exit, Exit C and Exit AES C, also are reset to zero as soon as reappears the phenomenon of CTVA (stage 290), that is to say a stimulation followed by an atrial detection in Pctva.

Figure 5:
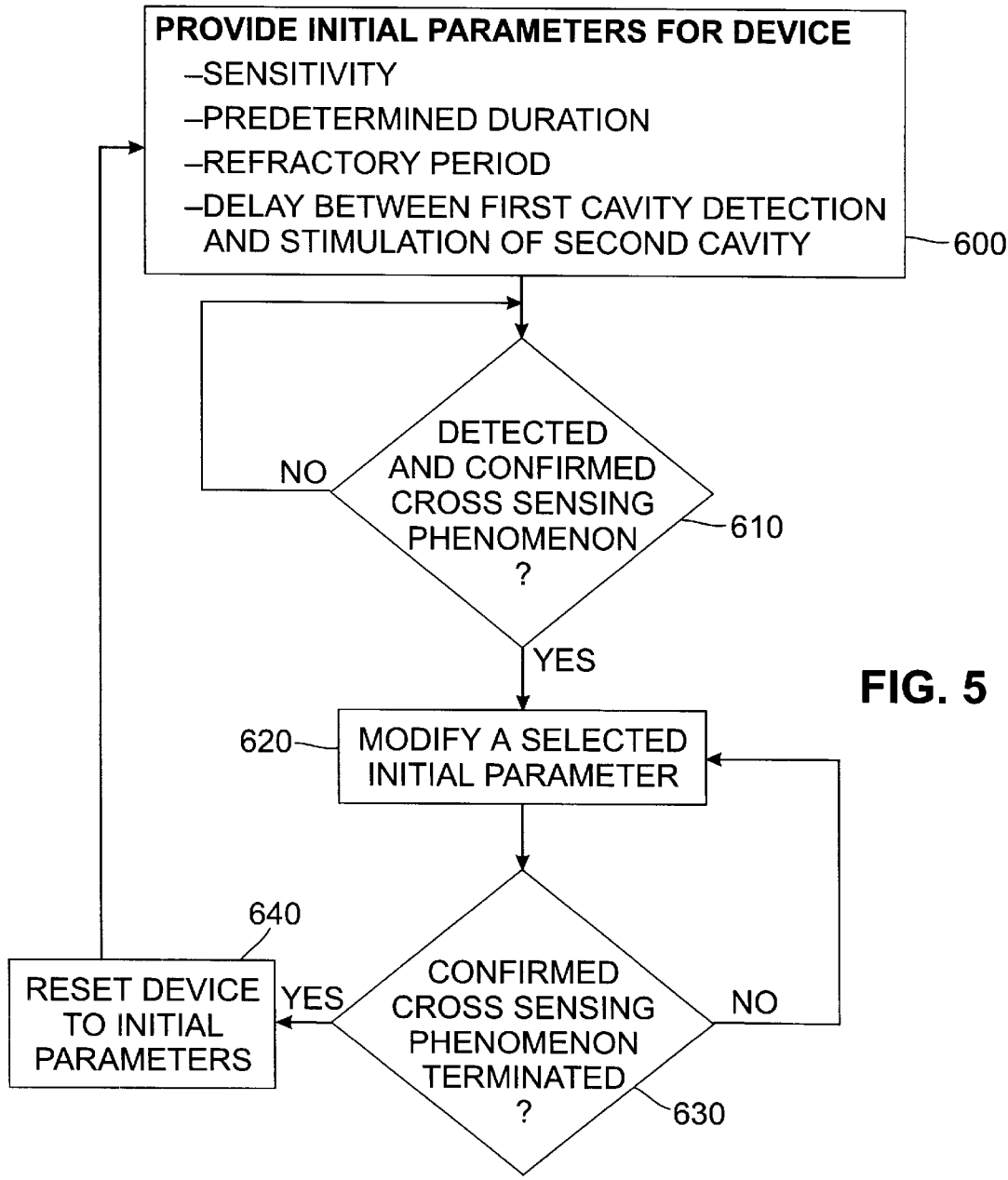
FIG. 5 is a schematic drawing of a device in accordance with the present invention.

As would be understood by a person of ordinary skill in the art, with reference to FIG. 5, may be implemented in an active implantable medical device 500 by use of discrete circuits (analog and/or digital circuits) or, alternatively, by a microprocessor based device 505 operating under software control. Indeed, software suitable to perform the above described operations is believed to be easily written by and within the abilities of a person of ordinary skill in the art and may be stored in suitable memory 510, e.g., ROM, or in firmware. Further, such software may be always functioning or selectively programmed to function only when desired, for example, in the case that the implanted device is determined to suffer from a cross-sensing phenomenon.

In addition, because the cross-sensing detection and confirmation need not require any additional circuits (other than the conventional circuits for acquiring cardiac event information 515 and conditioning those signals for processing by a microprocessor typically already exisiting in the device), software for processing such data in accordance with the present invention may advantageously be loaded into a RAM memory of microprocessor based device for use, for example, after the device is determined to suffer from cross-sensing. Thus, software may be transferred by conventional telemetry into an already implanted device, and then programmed to operate or not operate as appropriate or as needed. Such conventional medical devices that might use of the invention are known and include, for example, the CHORUS brand dual chamber cardiac pacemakers, which are available from ELA Medical S.A., Montrouge, France, the assignee hereof.

Figure 4:
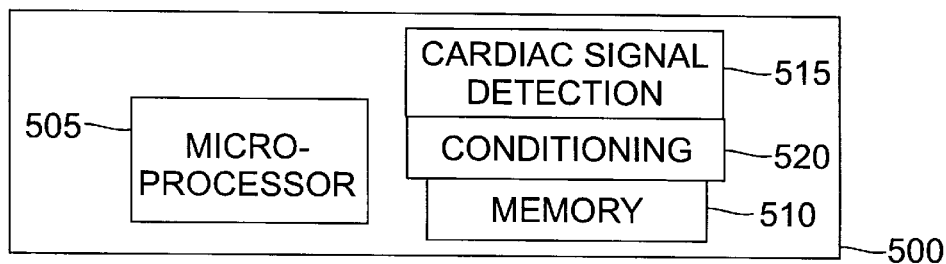
FIG. 4 is a flow chart illustrating a process for controlling a device in accordance with the present invention.

Referring to FIG. 4, a process is illustrated for modifying the operating characteristics of the device 500 to suppress a confirmed cross-sensing phenomenon and for resetting the device initial operating parameters when the cross-sensing phenomenon disappears. At step 600, the device 500 is provided with a set of initial operating parameters which includes, but is not limited to, a threshold voltage corresponding to a sensitivity of detection, a predetermined duration for comparing the interval between a stimulation in one chamber and a subsequent detection in the other chamber, a refractory period, and a delay between an event in the first cavity and the stimulation of the second cavity. At step 610, the device recognizes whether or not a cross-sensing phenomenon is confirmed to exist. If not, then the device 500 continues to operate according to its provided initial parameters. If a cross-sensing phenomenon does exist, then the device, at step 620, selects one of the initial parameters, e.g., the sensitivity or the refractory period, and modifies the selected parameter. At step 630, the device operating with the modified parameter determines whether the confirmed cross-sensing phenomenon has been suppressed. If not, then operation continues with another modification of an initial parameter (which may be a modification of the same parameter to a different value or of a different parameter or both) at step 620, and the test at step 630 is repeated. If the confirmed crosssensing phenomenon is determined to be suppressed at step 630, then the device operating parameters are reset at step 640 to the initial parameters, and the device 500 then return to its previously described operation.

One skilled in the art will appreciate that the present invention can be practiced by other than the described embodiments, which are presented for purposes of illustration and not of limitation.

We claim:

1. Apparatus for detecting cross sensing in an active implantable medical device, comprising:
   means for detecting spontaneous and stimulated cardiac events in a first cavity,
   means for stimulating a second cavity; and
   means for detecting and confirming a cross-sensing phenomenon comprising,
      means for detecting in the first cardiac cavity a first signal from a depolarization consecutive to a preceding stimulation of the second cavity,
      means for distinguishing the first signal from a signal resulting from a spontaneous activity in the first cardiac cavity, and
      means for detecting an extra-systole from the first cavity, said detected extra-systole occurring between a stimulation of the second cavity and detected a consecutive event in the first cavity; wherein said cross-sensing detecting and confirming means confirms said first signal detected as other than an extrasystole and a spontaneous activity in the first cardiac activity.

2. The device of claim 1, wherein the means for detecting cardiac events further comprises means for detecting atrial cardiac events and wherein the second cavity is an associated ventricular cavity.

3. The device of claim 1, in which the cross-sensing detecting and confirming means further comprises means for determining that an interval of time between the stimulation of the second cavity and the extra-systole of the first cavity is less than a predetermined duration, wherein the cross-sensing detecting and confirming means confirms the cross-sensing phenomenon in response to said interval being less than the predetermined duration.

4. The device of claim 1, in which the cross-sensing detecting and confirming means further comprises means for detecting the stability of an interval of time between the stimulation of the second cavity and the extra-systole of the first cavity, wherein the cross-sensing detecting and confirming means confirms the cross-sensing phenomenon in response to a detected stability.

5. The device of claim 4, in which the stability detecting means comprises means for varying a delay between the detection of an event in the first cavity and the stimulation of the second cavity, and for detecting the absence of a significant modification, with regard to these variations, of the interval of time between the stimulation of the second cavity and the extra-systole of the first cavity.

6. The device of claim 1, wherein the means for detecting spontaneous and stimulated cardiac events further comprises a refractory period associated with the first cavity and means for increasing the refractory period in response to a detected and confirmed cross-sensing phenomenon to suppress cross-sensing.

7. The device of claim 1, wherein the detecting means further comprises a threshold voltage corresponding to a sensitivity of cardiac event detection and further comprising means for adjusting the threshold voltage for increasing the sensitivity of the cardiac event detection means in the first cavity in response to a detected and confirmed cross-sensing to suppress cross-sensing.

8. The device of claim 1, further comprising a plurality of initial parameters, wherein said means for detecting and confirming said cross-sensing phenomenon further comprise means for modifying at least one of said initial parameters in connection with said confirmation; and means for detecting the end of the cross-sensing phenomenon and means for restoring to said initial value each of the plurality of initial parameters of the device modified by the cross-sensing means.

9. A process for detecting and confirming a cross-sensing phenomenon in an active implantable medical device having a dual cardiac chamber stimulation function, comprising:
   detecting cardiac events including spontaneous and stimulated cardiac events in a first cavity and stimulated cardiac events in a second cavity,
   detecting in the first cardiac cavity a first signal from a depolarization consecutive to a preceding stimulation of the second cavity, and
   distinguishing the detected first signal from a signal resulting from a spontaneous activity in the first cardiac cavity,
   detecting an extra-systole from the first cavity occurring between a stimulation of the second cavity and a detected consecutive event in the first cavity,
   detecting a sequence of a stimulation of the second cavity, an extra-systole, and a first signal for a predetermined number of successive second cavity stimulations, and
   detecting and confirming a cross-sensing phenomenon in response to a detected sequence of said detected extra-systoles linked to said second cavity stimulations.

10. The process of claim 9, in which detecting cardiac events further comprises detecting events in an atrial cavity as the first cavity and an associated ventricular cavity as the second cavity.

11. The process of claim 9, further comprising determining an interval of time between the stimulation of the second cavity and the extra-systole of the first cavity, determining that said interval is less than a predetermined duration, and confirming a cross-sensing phenomenon in response to the determined interval being less than the predetermined duration.

12. The process of claim 9 further comprising detecting an interval of time between the stimulation of the second cavity and the extra-systole of the first cavity, determining a stability of said interval over a period of time, and confirming a cross-sensing phenomenon in response to said determined stability.

13. The process of claim 12, in which determining the stability further comprises providing a delay between the detection of an event in the first cavity and the stimulation of the second cavity, varying the delay, and detecting an absence of a significant modification of the detected time interval in response to varying the delay.

14. A process for suppressing a cross-sensing phenomenon comprising:
   detecting cardiac events including spontaneous and stimulated cardiac events in a first cavity and stimulated cardiac events in a second cavity,
   detecting in the first cardiac cavity a first signal from a depolarization consecutive to a preceding stimulation of the second cavity,
   distinguishing the detected first signal from a signal resulting from a spontaneous activity in the first cardiac cavity,
   detecting an extra-systole from the first cavity occurring between a stimulation of the second cavity and a detected consecutive event in the first cavity,
   detecting a sequence of stimulation of the second cavity, an extra-systole, and a first signal for a predetermined number of successive second cavity stimulations, detecting and confirming a cross-sensing phenomenon in response to a detected sequence of said detected extra-systoles linked to said second cavity stimulation, providing a refractory period associated with the first cavity, and increasing the refractory period in response to a detected and confirmed crosssensing to suppress the cross-sensing.

15. A process for suppressing a cross-sensing phenomenon comprising:

detecting cardiac events including spontaneous and stimulated cardiac events in a first cavity and stimulated cardiac events in a second cavity, detecting in the first cardiac cavity a first signal from a depolarization consecutive to a preceding stimulation of the second cavity, distinguishing the detected first signal from a signal resulting from a spontaneous activity in the first cardiac cavity, detecting an extra-systole from the first cavity occurring between a stimulation of the second cavity and a detected consecutive event in the first cavity, detecting a sequence of stimulation of the second cavity, an extra-systole, and a first signal for a predetermined number of successive second cavity stimulations, detecting and confirming a cross-sensing phenomenon in response to a detected sequence of said detected extra-systoles linked to said second cavity stimulation, providing a sensitivity of cardiac event detection in the first cavity, and increasing the sensitivity of the cardiac event detection in response to a detected and confirmed cross-sensing to suppress said cross-sensing.

16. A process for operating a device for suppressing a cross-sensing phenomenon comprising: providing the device with a set of operating parameters having initial values, detecting cardiac events including spontaneous and stimulated cardiac events in a first cavity and stimulated cardiac events in a second cavity, detecting in the first cardiac cavity a first signal from a depolarization consecutive to a preceding stimulation of the second cavity, distinguishing the detected first signal from a signal resulting from a spontaneous activity in the first cardiac cavity, detecting an extra-systole from the first cavity occurring between a stimulation of the second cavity and a detected consecutive event in the first cavity, detecting a sequence of stimulation of the second cavity, an extra-systole, and a first signal for a predetermined number of successive second cavity stimulations, detecting and confirming a cross-sensing phenomenon in response to a detected sequence of said detected extra-systoles linked to said second cavity stimulation, wherein the detecting and confirming step further comprises varying at least one of said operating parameters, detecting an end of the crosssensing phenomenon in response to said varied parameter, and restoring to an initial value each of the operating parameters of the device modified by the detection and confirmation cross-sensing.

17. The process of claim 16 wherein varying the at least one operating parameter further comprises varying a delay between the detection of an event in the first cavity and the stimulation of the second cavity.

* * * * *

UNITED STATES PATENT AND TRADEMARK OFFICE
CERTIFICATE OF CORRECTION

PATENT NO.    : 5,978,708
DATED         : November 2, 1999
INVENTOR(S)   : Jean-Luc Bonnet & Laurence Geroux It is certified that error appears in the above-identified patent and that said Letters Patent is hereby corrected as shown below:

Column 1,
Line 8, delete "such those" and insert -- such as those -- therefor;
Line 31, delete "greater the" and insert -- greater -- therefor;
Line 64, delete "to decrease" and insert -- of decreasing-- therefor;

Column 3,
Line 2, delete "prevent" and insert -- present -- therefor;
Line 39, delete "extent the possible" and insert -- extent possible -- therefor;
Lines 40-41, delete "to apply" and insert -- the application of -- therefor;

Column 6,
Line 41, delete "solely of" and insert -- solely on --therefor;

Column 7,
Line 15, delete "state CTVA" and insert -- CTVA state -- therefor;
Line 37, delete "Csecurite" and insert -- Security C -- therefor;
Line 44, delete "Csecurite" and insert -- Security C -- therefor;

Column 8,
Line 32, delete "use" and insert -- make use -- therefor;

Column 9,
Line 4, delete "cross sensing" and insert -- cross-sensing -- therefor;
Line 23, delete "extrasystole" and insert -- extra-systole -- therefor; and

UNITED STATES PATENT AND TRADEMARK OFFICE
CERTIFICATE OF CORRECTION

PATENT NO.   : 5,978,708
DATED        : November 2, 1999
INVENTOR(S)  : Jean-Luc Bonnet & Laurence Geroux It is certified that error appears in the above-identified patent and that said Letters Patent is hereby corrected as shown below:

Column 11,
Line 7, delete "crosssensing" and insert -- cross-sensing -- therefor.

Signed and Sealed this

Seventeenth Day of August, 2004

JON W. DUDAS
*Acting Director of the United States Patent and Trademark Office*